United States Patent [19]

Petrille et al.

[11] 4,385,191

[45] May 24, 1983

[54] RECOVERY OF BF$_3$-FREE ALKYLPHENOL PRODUCT

[75] Inventors: Dennis G. Petrille; Chester G. Gunter, both of Naperville; Frederick S. Jerome, Elmhurst, all of Ill.

[73] Assignee: Standard Oil Company (Indiana), Chicago, Ill.

[21] Appl. No.: 105,391

[22] Filed: Dec. 19, 1979

[51] Int. Cl.$^3$ .................. C07C 37/68; C07C 37/14
[52] U.S. Cl. .................................. 568/792; 568/756; 568/787
[58] Field of Search .............. 568/756, 749, 787, 792

[56] References Cited

U.S. PATENT DOCUMENTS

| | | | |
|---|---|---|---|
| 2,655,544 | 10/1953 | McNulty et al. | 568/792 |
| 3,000,964 | 9/1961 | Milligan | 568/792 |
| 3,360,464 | 12/1967 | Otto | 252/51.5 A |
| 4,017,548 | 4/1977 | Petrille | 568/792 |

FOREIGN PATENT DOCUMENTS

| | | | |
|---|---|---|---|
| 481909 | 3/1938 | United Kingdom | 568/792 |
| 1159368 | 7/1969 | United Kingdom | 568/792 |

*Primary Examiner*—Werren B. Lone
*Attorney, Agent, or Firm*—Gunar J. Blumberg; William T. McClain; William H. Magidson

[57] ABSTRACT

Drastic molecular weight degradation of a p-(polybutyl-substituted phenol occurs when it is heated above 65° C. in the presence of BF$_3$-phenolate catalyst used in the preparation of said substituted phenol by the alkylation of phenol with a butylene polymer of 500 to 3000 molecular weight. Such molecular weight degradation can be substantially suppressed by providing 20 to 30 weight percent dissolved phenol in the mixture resulting from such catalytic alkylation reaction and then rapidly heating the mixture with such amount of dissolved phenol to a temperature of from 182° C. up to 200° C. at extant atmospheric pressure whereat the catalyst dissociates and liberated BF$_3$ is stripped out by phenol vapors.

3 Claims, No Drawings

RECOVERY OF BF$_3$-FREE ALKYLPHENOL PRODUCT

FIELD OF INVENTION

This invention relates to the continuous dissociation of BF$_3$-phenolate catalyst and removal of BF$_3$ from the fluid product containing a p-alkyl-substituted phenol obtained from the BF$_3$-phenolate catalyzed alkylation of phenol with a 500 to 3000 molecular weight butylene polymer under conditions which suppress molecular weight degradation of the desired alkyl-substituted phenol by either BF$_3$ or BF$_3$-phenolate. Such dissociation and BF$_3$ removal are accomplished by subjecting the mixture resulting from said alkylation to rapidly vaporize phenol dissolved in the fluid alkylation product in an amount of from 20 to 30 weight percent in a system open to the atmosphere that is at 0 gauge pressure. By such operations the vaporized phenol sweeps BF$_3$ from the fluid alkylation product under temperature conditions which otherwise would cause drastic molecular weight degradation of the desired p-alkylphenol.

STATE OF THE ART

British patent specification No. 481,909, published in 1938, teaches the para-directing effect of BF$_3$phenolate catalyst on the alkylation of phenols with C$_5$-C$_{12}$ mono-olefinic hydrocarbons and low molecular weight polymers thereof at reaction temperatures in the range of 0°-100° C.

U.S. Pat. No. 2,655,544, issued Oct. 13, 1953, extends such teaching with respect to BF$_3$-phenolate catalysis to the use of C$_{18}$-C$_{24}$ mono-olefinic hydrocarbons to alkylate phenol.

U.S. Pat. No. 3,360,464, issued December 1967, further extends such BF$_3$-phenolate catalysis to the use of 500-3000 molecular weight (i.e., about C$_{36}$ to about C$_{214}$) mono-olefinic hydrocarbons, which are polymers of ethylene, propylene, butylene, isobutylene or amylene, to alkylate phenol.

British Pat. No. 1,159,368, published July 23, 1969, confirms by infrared analysis that the BF$_3$-phenolate catalysis of phenol alkylation with 700-280,000 molecular weight polymer of propylene or isobutylene results in an alkylphenol product which is more than 95 percent p-alkyl-substituted.

In the foregoing patents, whenever removal of BF$_3$ from the fluid alkylation product is mentioned, the suggested and/or illustrated techniques for such removal are by water and/or caustic washing of such fluid product or by treatment thereof with ammonia or amine to form a filterable ammonium-BF$_3$ complex. The first mentioned British Patent also states that BF$_3$ was removed from the fluid alkylation product and recycled to the alkylation reaction but it does not illustrate how such recovery and recycle were accomplished. However, U.S. Pat. No. 3,000,964, issued Sept. 19, 1961, which is directed to the preparation and recovery of the alkylphenol product from a C$_3$ to C$_{20}$ mono-olefinic hydrocarbon and phenol, discloses that prior to its inventive technique for BF$_3$ removal from the resulting fluid alkylation product there was no satisfactory method for removal and recovery of BF$_3$ in reusable form from such fluid product.

The BF$_3$ removal and recovery technique of said 1961 patent involves combining with such fluid alkylation product from 30 up to 200 weight percent thereon of an inert hydrocarbon entrainer having a boiling point in the range of 30° to 200° C. to lower the boiling temperature of said fluid product to the range of from 50° C. up to 175° C., preferably 100° C. to 175° C. The resulting mixture is refluxed in a distillation column at such reduced boiling temperature under conditions which permit the entrainer vapors to carry BF$_3$ gas to a condenser wherein the entrainer is condensed. The entrainer-free BF$_3$ gas is discharged into molten phenol which absorbs BF$_3$ as BF$_3$-phenolate. The phenol containing the BF$_3$-phenolate is recycled to the alkylation reaction.

British patent specification No. 1,159,368, establishes that BF$_3$-phenolate catalyzed alkylations of phenol with a polymeric hydrocarbon consisting predominantly of butylene units (e.g., units from 1-butene, 2-butene and isobutylene) causes fragmentation of the polymeric hydrocarbon so that the resulting p-alkylphenol has a molecular weight differing from the theoretical molecular weight by from 10% up to 72% depending upon the reaction temperature. Such fragmentation and lowering of molecular weight of the p-alkylphenol product increases as the reaction temperature increases. For example, using the same polybutene polymer as reactant with phenol at a reaction temperature of 22° C. the fragmentation results in a molecular weight decrease from the theoretical of only 9.75%; at a reaction temperature starting at 26.7° C. and increasing to 37.8° C. the molecular weight decrease from the theoretical is 51.8%; and at a reaction temperature starting at 60° C. and increasing to 71° C. the molecular weight decrease from the theoretical is 72.1%.

It has been discovered that when the mixture resulting from the alkylation of phenol with a polybutene in the presence of BF$_3$-phenolate catalyst is heated to a temperature of 70° C. and higher the p-alkylphenol product continues to decrease drastically in molecular weight. Thus such mixture, even diluted with a hydrogen entrainer could not be heated to and maintained at reflux temperature which would be above 70° C. without causing the further decrease in molecular weight of the p-alkylphenol product.

U.S. Pat. No. 3,692,844 discloses the BF$_3$-phenol catalyzed reaction between phenol and a terpene (e.g., alpha-pinene, beta-pinene, 3-carene, and turpentine using at least two moles of phenol per mole of terpene, from 0.05 to 1.5 weight percent BF$_3$ on the terpene and a reaction temperature of from 50° C. up to 130° C. The patent further discloses that when the reaction is carried out below 50° C. undesirable phenolic ethers are formed and when carried out above 130° C. the reaction mixture becomes dark in color. Then after said reaction (by which one mole of terpene links two moles of phenol) the reaction mixture is heated under reduced pressure in distillation apparatus to cause any unreacted phenol to distill off and carry with it all of the BF$_3$. There is no evidence in this patent that the terpene-phenol product decreases in molecular weight at temperatures between 50° C. and 130° C. in the presence of the BF$_3$-phenolate catalyst. Since BF$_3$-phenolate dissociates at about 93° C. and phenol boils above 181° C., the reduced pressure distillation must have been carried out at a temperature of at least 93° C. and no molecular weight degradation of the terpene-phenol was reported.

A novel technique has now been discovered for BF$_3$ removal from the viscous fluid alkylation product obtained by phenol alkylation with 500-3000 M.W. polymer of propylene or butylene in the presence of BF$_3$- phenolate catalyst. The novel technique does not use a hydrocarbon entrainer or any other material to lower the boiling point of the fluid alkylation product and does not involve refluxing a diluted, lower boiling point mixture in a distillation column. Rather, the present inventive novel technique for $BF_3$ removal and recovery involves the simultaneous and rapid thermal dissociation of the $BF_3$-phenolate catalyst and vaporization of phenol at ambient pressure whereby phenol vapors strip dissociated $BF_3$ gas therefrom leaving a $BF_3$-free portion of the fluid alkylation reaction product. To accomplish such stripping of dissociated $BF_3$ gas the phenol content of the viscous fluid alkylation reaction mixture being heated should be in the range of from 20 up to 30 weight percent.

SUMMARY OF THE INVENTION

In its simplest form the present inventive process for the removal of $BF_3$ from the fluid reaction mixture produced by the $BF_3$-phenolate catalyzed alkylation of phenol with a butylene polymer of molecular weight in the range of from 500 up to 3000 comprises subjecting such fluid alkylation mixture containing 20 to 30 weight percent dissolved phenol to continuous heating under fluid flow conditions to a temperature in the range of from 182° C. up to 200° C. Such 20–30 percent phenol content can be provided by the use of appropriate excess phenol reactant or by dissolving additional liquid phenol in the fluid alkylation reaction mixture when the amount of phenol reactant used in the alkylation reaction does not provide the required 20 to 30 percent concentration. Such removal of $BF_3$ can be conveniently conducted at atmospheric pressure. Recovery of $BF_3$ can be readily made by cooling the mixture of $BF_3$ gas and phenol vapors to provide liquid phenol condensate which absorbs $BF_3$ gas.

Such continuous heating under fluid flow conditions to 182° to 200° C. and the 20 to 30 weight percent dissolved phenol concentration are both critical to the successful removal of $BF_3$. The continuous heating under fluid flow provides the technical effects of substantially instantaneous dissociation of $BF_3$-phenolate catalyst and vaporization of phenol in small incremental portions of the fluid. The technical effect of the 20 to 30 weight percent phenol concentration is that such amount of phenol upon vaporization rapidly sweeps the dissociated $BF_3$ gas from the small increment of the hot fluid. The combination of those technical effects prevents the $BF_3$-phenolate induced drastic molecular weight degradation of the desired high molecular weight alkylphenol product which, as later established, occurs under batchwise heating of the fluid alkylation reaction at a temperature as low as 70° C. regardless of the phenol content of the fluid alkylation reaction mixture.

For process economics of commercial operation and for such operation to prevent contamination of the atmosphere with $BF_3$ gas and phenol vapors it is important to recover the $BF_3$ and associated phenol vapors from the present inventive process.

Such removal of $BF_3$ and the recovery of both the removed $BF_3$ gas and vaporized phenol are conveniently conducted at ambient pressure in the combination of interconnected zones consisting essentially in sequence of either (1) a bottom partial-reboiling zone, a stripping zone and a condensing zone or (2) a bottom partial-reboiling zone, a stripping zone, a rectifying zone, and a condensing zone. The fluid reaction mixture together with 20 to 30 weight percent phenol dissolved therein is continuously in small incremental portions fed to the stripping zone and rapidly heated to a temperature in the range of from 182° C. up to 200° C. to dissociate the $BF_3$-phenolate catalyst and vaporize phenol. The heat for such dissociation and vaporization is provided by heating to a temperature in the range of from 225° C. up to 275° C. the $BF_3$-free portion of the fluid reaction mixture in the partial-reboiling zone flowing thereto from the stripping zone. Such heating of said $BF_3$-free fluid generates hot vapors which flow upward into the stripping zone and contact the fluid fed to said zone. The dissociated $BF_3$ gas and phenol vapor issuing from the stripping zone flow to the condensing zone operated at a temperature below the boiling point but above the melting point of phenol to condense phenol vapors to liquid in contact with $BF_3$ gas thereby reforming $BF_3$-phenolate in liquid phenol. Such condensate and additional make-up phenol are charged to the alkylation reaction. In this case no rectifying zone is needed. Such condensate can also be totally recycled to the $BF_3$ removal process and in this case a recitifying zone is needed between the stripping zone and the condensing zone. Such total reflux of the condensate is to the rectification zone wherein $BF_3$ enrichment occurs. Upon cooling said mixture in the condensing zone two phases, a liquid phase of liquid phenol saturated with $BF_3$ and a $BF_3$ gas phase, form. The $BF_3$ saturated liquid phenol is recycled to rectifying zone and the $BF_3$ gas is separated and absorbed in the phenol used in the alkylation reaction.

The presence of 20 to 30 weight percent of phenol in the fluid alkylation reaction mixture fed to the stripping zone is essential for rapid sweeping of dissociated $BF_3$ gas from the fluid mixture which is rather viscous even at the temperatures in the range of 182° C. up to 200° C. Heating of small incremental portions of the feed to the stripping zone to such temperatures is essential for rapid dissociation of $BF_3$-phenolate without causing drastic molecular weight degradation of the desired high molecular weight alkylphenol product which would otherwise occur when large portions of the fluid reaction mixture, with or without the 20 to 30 weight percent of dissolved phenol, are heated (i.e., batchwise heating). Such drastic molecular weight degradation can occur under batchwise heating (heating of large quantities) of the before defined fluid alkylation reaction mixture at a temperature of about 70° C. For example, batchwise heating to a temperature of 70°–71° C. of the fluid alkylation reaction mixture containing an 1823 M.W. alkyl-substituted (substituent from butylene polymer) phenol product in the presence of the $BF_3$-phenolate catalyst causes drastic molecular weight degradation of the product amounting to about 72 percent.

The $BF_3$-phenolate catalyzed alkylation of phenol with the 500–3000 molecular weight mono-olefinic butylene polymer inherently produced a rather viscous fluid reaction mixture because of the highly viscous nature of the 500–3000 molecular weight polymer. Such polymers have a viscosity in the range of 400 to 200,000 centistokes at 37.5° C. In contrast, the $C_3$–$C_{24}$ (42–336 M.W.) mono-olefinic hydrocarbons have a much lower viscosity at 37.5° C. For example, a 300 M.W. mono-olefin has a 20 centistoke viscosity at 37.5° C. Since the viscosity characteristics of the fluid alkylation reaction mixture are associated with the mono-olefinic hydrocarbon used to alkylate phenol, the fluid alkylation reaction mixture from the use of the 500–3000 molecular weight mono-olefinic polymer presents a problem with respect to the escape of BF$_3$ gas from the viscous liquid. The rapid dissociation of BF$_3$-phenolate and vaporization of phenol achieved by the present inventive process overcomes said problem as well as the problem of drastic molecular weight degradation which would occur at temperatures needed for dissociation of BF$_3$-phenolate catalyst.

Alkylation of phenol with the 500–3000 M.W. viscous liquid butylene polymer can be conducted at a temperature in the range of 0° to 60° C. in the presence of BF$_3$-phenolate catalyst using at least one mole of phenol per mole of the viscous liquid polymer. Because the desired high molecular weight alkyl-substituted phenol product is used as an intermediate for the preparation of addition agents for petroleum fractions (fuels and lubricant oils), the alkylation is conducted in the presence of a refined petroleum fraction lubricant oil such as neutral white oils and oils of the SAE-5W to SAE-40 types. The amount of such reaction diluent oil so used amounts to 30 to 70 weight percent of the polymer reactant. While the diluent lubricating oil reduces the viscosity of the fluid alkylation reaction mixture, such oil diluents do not, of course have the boiling point characteristics of the before mentioned hydrocarbon entrainers.

Use of such lubricant oil reaction diluent has, according to British patent specification No. 1,159,368, the further advantage of permitting the use of alkylation reaction temperatures of from 45° C. up to 60° C. without an undesirable increase in BF$_3$-phenolate induced fragmentation of the butylene polymer reactant or molecular weight degradation of the desired high molecular weight alkyl-substituted phenol.

The viscous fluid alkylation reaction mixture used in the present inventive BF$_3$ removal process is, in view of the foregoing, prepared at a temperature in the range of from 45° C. up to 60° C. by the use of from 1.0 to 6.0 moles of phenol and from 0.05 up to 0.5 moles of BF$_3$-phenolate catalyst per mole of butylene polymer of number average molecular weight ($\overline{M}_n$) in the range of from 500 up to 3000 in the presence of from 30 up to 70 weight percent of the before described lubricant oil diluent based on said polymer reactant. Such viscous fluid alkylation reaction mixture, in addition to the lubricant oil diluent, BF$_3$-phenolate catalyst and unreacted phenol also contains the desired alkylphenol product whose alkyl-substituent is in the range of from 475 up to 2800 $\overline{M}_n$, lower molecular weight (C$_3$–C$_{12}$) alkyl-substituted phenol as a by-product and a 500–3000 $\overline{M}_n$ alkane hydrocarbon.

The desired alkylphenol product having the alkyl-substituent of 475–2800 $\overline{M}_n$ instead of 500–3000 $\overline{M}_n$ and the by-product lower molecular weight alkylphenol by-product result from the inherent fragmentation of the butylene polymer reactant by the BF$_3$-phenolate catalyst at the 45° to 60° C. reaction temperature. The use of lower reaction temperature, e.g., 0° C. to 30° C., can diminish such fragmentation but at the expense of slower reaction rates which are not commercially attractive. The fragments of the butylene polymer are also mono-olefinic and react with phenol to produce the lower molecular weight alkylphenol by-product.

The 500 to 3000 $\overline{M}_n$ alkane component of the viscous liquid reaction mixture is associated with and comes from the preparation of the butylene polymer reactant. Such polymeric reactants of the 500–3000 $\overline{M}_n$ range are commercially available from the polymerization of a butylene or C$_4$ petroleum fraction (e.g., isobutylene alone or in admixture with other butenes and butane) in the presence of a Friedel-Crafts type catalyst, generally aluminum chloride. The product from such polymerization, after catalyst removal and fractions boiling up to the gasoline range, contain from 15 to 5 weight percent of the 500 to 3000 $\overline{M}_n$ alkane entities and from 85 to 95 percent of mono-olefinic entities. Such mono-olefinic entities comprise molecules having a saturated chain terminated by a single mono-unsaturated unit. Said saturated chain portion of the molecules have repeating or butyl units (from butylene). The mono-olefinic entities add, through their terminal unsaturated unit, mainly (over 95%) to the p-ring carbon of phenol and the hydrogen from said ring carbon saturates the double bond. Thus the alkylation product of high molecular weight from the use of butylene polymer is a 475 to 2800 $\overline{M}_n$ alkyl-substituted, not an alkenyl-substituted, phenol whose alkyl-substituent contains repeating butyl (hence polybutyl) units.

The high boiling characteristics of the above 500 to 3000 $\overline{M}_n$ alkane hydrocarbon entities, as is the case with the high boiling characteristics of the lubricant oil reaction diluent, do not permit such alkane entities to function as reflux temperature lowering diluents or BF$_3$ gas entrainers.

SPECIFIC EMBODIMENTS OF THE INVENTION

The partial condensing zone can be operated at a temperature to provide a liquid condensate at or above phenol's melting (42°–43° C.) temperature but preferably is operated to provide a condensate of a temperature in the range of from 43° C. up to 50° C. when all of the phenol condensate containing reformed BF$_3$-phenolate is recycled to the alkylation reaction. However, when the phenol condensate saturated with BF$_3$ is returned as total reflux to the rectification zone, the condensing zone can be operated to provide a liquid condensate in the range of from 60° C. up to 150° C.

The stripping zone portion of the combined interconnected zones should have at least two trays each of at least 50% separation efficiency. The feed will be to the top of such two tray efficiency stripping zone. When the rectifying zone is used with total reflux of the phenol condensate, the rectifying zone should have at least the efficiency of one of 50% separation efficiency trays. The combination of stripping zone and rectifying zone can be a single column equivalent to the three 50% separation efficiency trays and the feed thereto will be to the second from the bottom tray.

The viscous liquid alkylation reaction mixture used in the present inventive BF$_3$ removal and recovery process results from the BF$_3$-phenolate catalyzed reaction of the 500–3000 M.W. butylene polymer of 5–15% alkane and 95–85% alkene content with phenol in the respective reactant molar ratio of 1.0:1.0 to 1.0:6.0. Such 1.0 to 6.0 moles of phenol contain the 0.05 to 1.0 mole of BF$_3$ for the catalyst obtained by adding BF$_3$ gas to liquid phenol at a temperature of 45° to 55° C. The alkene molecular species are substantially completely consumed in the alkylation reaction. Thus the resulting viscous liquid reaction mixture will contain the following components in the indicated weight percent concentration ranges:

| | |
|---|---|
| 500–3000 M.W. alkane hydrocarbon | 1–2% |

-continued

| | |
|---|---|
| 475–2800 M.W. alkyl-substituted phenol product | 20–50% |
| $C_3$–$C_{12}$ alkylphenol by-product mixture | 0.5–8% |
| Unreacted phenol | 1.0–30% |
| $BF_3$ | 0.1–4% |
| Diluent oil | 70–30% |

The following compositions are typical viscous fluid alkylation reaction mixtures which can result from the indicated reactants and their molar reactant ratios. The quantity of diluent oil is that to provide an ultimate product concentration of 35% or 50% by weight.

Composition I (A) From 1.0 mole 500 M.W. butylene polymer of 5% alkane (500 M.W.) content, 1.4 mole phenol and 0.1 mole $BF_3$:

| (B) | Liquid reaction mixture: | Wt. % |
|---|---|---|
| | 500 M.W. alkane | 1.2–2.3 |
| | 450 M.W. alkyl-substituted phenol product | 24.6–45.3 |
| | Alkylphenol by-product | 3.6–6.6 |
| | Unreacted phenol | 1.2–2.3 |
| | $BF_3$ | 0.3–0.6 |
| | Diluent oil | 69.0–43.0 |

Composition II (A) From 1.0 mole 2600 M.W. butylene polymer of 10% alkane (2600 M.W.) content, 2.7 moles phenol and 0.5 mole $BF_3$:

| (B) | Liquid reaction mixture: | Wt. % |
|---|---|---|
| | 2600 M.W. alkane | 2.1–3.8 |
| | 2340 M.W. alkyl-substituted phenol product | 24.6–45.2 |
| | Alkylphenol by-product | 3.7–6.7 |
| | Unreacted phenol | 1.2–2.1 |
| | $BF_3$ | 0.4–0.7 |
| | Diluent oil | 68.0–41.5 |

Composition III (A) From 1.0 mole 3000 M.W. butylene polymer of 15% alkane (3000 M.W.) content, 3.0 moles phenol and 0.19 mole $BF_3$:

| (B) | Liquid reaction mixture: | Wt. % |
|---|---|---|
| | 3000 M.W. alkane | 4.6–8.5 |
| | 2800 M.W. alkyl-substituted phenol product | 24.8–46.2 |
| | Alkylphenol by-product | 2.2–4.1 |
| | Unreacted phenol | 1.6–3.2 |
| | $BF_3$ | 0.1–0.2 |
| | Diluent oil | 66.4–37.8 |

Composition IV (A) From 1.0 mole 2200 M.W. butylene polymer of 8% alkane (2200 M.W.) content, 3.0 moles phenol and 0.28 mole $BF_3$:

| (B) | Liquid reaction mixture: | Wt. % |
|---|---|---|
| | 2200 M.W. alkane | 1.8–3.4 |
| | 1500 M.W. alkyl-substituted phenol product | 25.2–47.3 |
| | Alkylphenol by-product | 0.7–1.3 |
| | Unreacted phenol | 1.8–3.5 |
| | $BF_3$ | 0.3–0.5 |

-continued

| (B) | Liquid reaction mixture: | Wt. % |
|---|---|---|
| | Diluent oil | 70.2–44.0 |

Composition V (A) From 1.0 mole 3000 $\overline{M}_n$ butylene polymer, 6.0 moles phenol and 0.5 mole $BF_3$:

| (B) | Liquid reaction mixture: | Wt. % |
|---|---|---|
| | 3000 M.W. alkane | 8.2–11.3 |
| | 2890 M.W. alkylphenol product | 31.7–43.6 |
| | Alkylphenol by-products | 5.4–7.5 |
| | Unreacted phenol | 3.4–4.7 |
| | $BF_3$ | 0.5–0.6 |
| | Diluent oil | 50.7–32.3 |

For the practice of the present inventive $BF_3$ removal technique, the feed to the atmospheric stripping operation should contain 20 to 30, and preferably 25, weight percent dissolved phenol. Such dissolved phenol can come from the use of excess phenol reactant or from the addition of phenol to the liquid alkylation reaction mixture. Such 20–30% phenol includes both the unreacted phenol and phenol of the $BF_3$-phenolate catalyst.

The following three Comparative Examples illustrate the molecular weight degradation of the alkyl-substituent in the stripping operation when the fluid alkylation reaction mixture feed does not contain the 20–30 weight percent phenol. These three Comparative Examples and the Illustrative Example are conducted with a two tray glass distillation column having two trays of about 50% separation efficiency and having a partial-reboiling zone volume of about 1000 millimeters. The partial reboiling zone is initially charged with about 500 milliliters of $BF_3$-free fluid alkylation reaction mixture otherwise corresponding to the fluid alkylation reaction mixture charged to the bottom tray (first tray) in the column. Means are provided for measuring the temperature of the fluid in the reboiling zone, and on the first and second trays. Heat is supplied to the reboiling zone by an electric mantle. Fluid is removed from the partial-reboiling zone by a pump at the rate which maintains a level substantially equal to the level of initial fluid charge thereto. The first fluid withdrawn from the partial-reboiling zone, equal in volume to the volume of the initial charge to said zone, is separately collected as representative of the $BF_3$-free fluid initially charged to said zone. Thereafter fluid withdrawn from said zone is collected as representative of the alkylation reaction mixture from which $BF_3$ was stripped.

The $BF_3$-free alkylation reaction mixture initially charged to the partial-reboiling zone had been obtained, in each case, from the alkylation conducted in the following manner. The $BF_3$-phenolate (0.1 mole) of phenol catalyzed alkylation is conducted at a temperature of 50° C. The molar ratio of phenol to copolymer of isobutylene and normal butenes of polymer molecular weight of 2200 is 3:1. The light mineral oil (e.g. SAE-5W base oil), to reduce the viscosity of the reaction mixture, is used in a weight ratio of about 2:1 of polymer to oil. Upon completion of the reaction, about two hours, the reaction mixture (temperature of 54°–55° C.) is neutralized (bromthymol blue indicator) with ammonia and filtered to remove $NH_3$-$BF_3$ solids. This $BF_3$- free alkylation mixture is the initial 500 milliliter charge to the partial-reboiler zone.

In the first Comparative Example, the two tray column is fitted with a steam cooled (160° C.) reflux condenser. Condensate is recycled as reflux to the column and non-condensed materials are vented to the atmosphere. In the remaining three examples the column is fitted with a steam cooled (exit temperature of 100° C.) inclined side arm condenser (no reflux) for collection of phenol condensate and the condensate collector is vented to the atmosphere. Hence all the examples are conducted at extant atmosphere pressure.

In each of the foutr examples the fluid alkylation reaction mixture, prepared as described above, is charged through a preheater to heat the fluid to a temperature in the range of 60°-65° C. from 54°-55° C. and then to the first (bottom) tray when the fluid in the partial-reboiling zone is at the higher temperature later given. The lower temperature of the partial reboiling zone is the steady state temperature of continuous operation.

The molecular weight and concentration of the copolymer subsubstitued phenol product are determined for such product contained in both the BF$_3$-phenolate containing alkylation reaction mixture and its stripped fluid product removed from the partial-reboiling zone. The phenol content of the alkylation reaction mixture and the BF$_3$ content of the stripped product are determined. These determinations: phenol concentration in the feed to the stripping zone resulting from added phenol; temperature range during operation for the top (second) tray, feed (first) tray and partial-reboiling zone; the molecular weight of polymer alkylated phenol and its concentration, are reported in the following table.

advantage in adding such excess amounts of phenol because it must be stripped from the BF$_3$-free alkylation reaction mixture before the product polymer alkylated phenol is suitable for further use. The minimum phenol concentration in the feed charged to the atmospheric pressure continuous BF$_3$ stripping is about 20 weight percent for prevention of molecular weight degradation of the 475–2800 M.W. polymer alkylated phenol product.

The invention claimed is:

1. A method of removing BF$_3$ from the fluid reaction mixture produced by the alkylation of phenol with a butylene polymer of from 500 up to 3000 $\overline{M}_n$ at a temperature in the range of from 45° C. up to 60° C. in the presence of BF$_3$-phenolate catalyst and lubricant oil diluent wherein 1.0 to 6.0 moles of phenol and 0.05 to 0.5 mole catalyst are present per mole of said polymer and said diluent is present in the range of from 30 up to 70 weight percent of said polymer; which method comprises heating such fluid alkylation reaction mixture containing 20 to 30 weight percent dissolved phenol consisting essentially of excess phenol reactant or a combination thereof with post reaction added phenol under continuous fluid flow conditions to a temperature in the range of from 182° C. up to 200° C. at extant atmospheric pressure to dissociate BF$_3$ gas from the catalyst and sweep said gas from the heated fluid with vaporized phenol.

2. The BF$_3$ removal method of claim 1 and the recovery of BF$_3$ dissociated and phenol vaporized at said temperature of from 182° to 200° C. which comprise the process of continuously introducing said fluid alkylation reaction mixture containing the 20 to 30 weight percent dissolved phenol as feed into the stripping zone portion of the combination of interconnected zones consisting essentially in the sequence of a bottom partial-reboiling zone, a stripping zone, and a top partial-condensing zone; wherein:

(a) the BF$_3$-free liquid portion of said fluid feed flowing from said stripping zone to said partial-reboiling zone is heated therein to a temperature in the range of from 225° C. up to 275° C. to generate vapors;

(b) the vapors generated from said partial reboiling zone flow upward therefrom into the stripping zone to heat the fluid feed thereto to said temperature of 182° to 200° C. and simultaneously dissoci-

| ATMOSPHERIC PRESSURE STRIPPING OF BF$_3$ | | | | |
|---|---|---|---|---|
| Stripping Conditions | Comparative Example No. | | | Illustrative |
| and Components | 1 | 2 | 3[(4)] | Example |
| Feed Rate[(1)] g/min | 3.4 | 3.4 | 3.58 | 3.58 |
| Feed Components: | | | | |
| Initial Phenol, Wt. % | 4.6 | 4.6 | 4.6 | 4.6 |
| Total Phenol After Addition, Wt. % | 4.6 | 10 | 10 | 25 |
| Polymer Alkylated Phenol, Wt. %[(2)] | 44.6 | 46.7 | 42.2 | 42.5 |
| Polymer Alkylated Phenol, N.W.[(2)] | 1725 | 1744 | 1732 | 1700 |
| Top Tray Temperature, °C. | 278–138[(5)] | 194 | 196 | 188 |
| Bottom Tray Temperature, °C. | 219–297 | 196 | 199 | 200 |
| Partial-Reboiling Zone Temperature, °C. | 247–225 | 278 | 275 | 245 |
| Effluent From Stripping: | | | | |
| Polymer-Alkyl Sub. Phenol, Wt. %[(3)] | 36.5 | 40.0 | 41.9 | 41.9 |
| Polymer-Alkyl Sub. Phenol, M.W.[(3)] | 1413 | 1480 | 1400 | 1700 |
| BF$_3$, Wt. % | 0 | 0 | 0 | 0 |

[(1)]Feed rate through preheating and to Feed Tray.
[(2)]From BF$_3$-free sample steam stripped of phenol and C$_3$–C$_{12}$ alkylphenols.
[(3)]From sample steam-stripped of phenol and C$_3$–C$_{12}$ alkylphenols.
[(4)]Feed to Top Tray.
[(5)]Temperatures dropped throughout stripping.

Although the extant atmospheric pressure stripping successfully removed BF$_3$ in each of the four examples, there were substantial differences in molecular weight reduction of the desired polymer-alkylated phenol product in the operations of Comparative Examples Nos. 1, 2, and 3 but no molecular weight changes occurred from the operation of the Illustrative Example. The use of vaporized phenol to aid in the stripping of BF$_3$ from the viscous alkylation reaction mixture (the feed in the four examples has a viscosity of about 3000 centipoise at 52° C.) is, in general, effective in preventing molecular weight degradation in feed phenol concentrations above 30 weight percent but there is no ate the catalyst and vaporize phenol by contact with said feed;

(c) the mixture of BF$_3$ gas and phenol vapors issuing from the stripping zone flow to the condensing zone cooled to condense phenol as a liquid in the present of and to absorb BF$_3$ gas for in situ reforming of BF$_3$-phenolate dissolved in liquid phenol at a temperature in the range of from 43° C. up to 60° C.; and (d) recycling said 43°–60° C. temperature phenol condensate solution of catalyst to the alkylation reaction.

3. The BF$_3$ removal and recovery process of claim 2 wherein said combination of interconnected zones has a rectification zone between said stripping and condensing zones, the condensing zone is cooled to provide a liquid phenol condensate solution of BF$_3$-phenolate catalyst at a temperature in the range of 60° up to 150° C., said condensate is fed as reflux liquid to the rectification zone for enrichment of the gas-vapor mixture therein with respect to BF$_3$ gas, and withdrawing only BF$_3$ gas from the condensing zone for absorption in liquid phenol charged to the alkylation reaction.

* * * * *

UNITED STATES PATENT OFFICE
CERTIFICATE OF CORRECTION

Patent No. 4,385,191           Dated May 24, 1983

Inventor(s) Dennis G. Petrille, Chester G. Gunter, Frederick S. Jerome

It is certified that error appears in the above-identified patent and that said Letters Patent are hereby corrected as shown below:

| Patent Column | Line | |
|---|---|---|
| 1 | 26 | "BF$_3$phenolate" should read --BF$_3$-phenolate |
| 2 | 38 39 | "hydrogen" should read --hydrocarbon-- |
| 9 | 13 | "foutr" should read --four-- |

Signed and Sealed this

Fifteenth Day of November 1983

[SEAL]

Attest:

GERALD J. MOSSINGHOFF

Attesting Officer   Commissioner of Patents and Trademarks

Gunar J. Blumberg